United States Patent
Hamada et al.

(10) Patent No.: US 10,173,960 B2
(45) Date of Patent: Jan. 8, 2019

(54) COMPOSITION

(71) Applicant: DAIKIN INDUSTRIES, LTD., Osaka (JP)

(72) Inventors: Tomohito Hamada, Osaka (JP); Makoto Matsuura, Osaka (JP); Asako Yoshiyama, Osaka (JP); Akihiro Gotou, Osaka (JP); Manaho Miyazaki, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/564,927

(22) PCT Filed: Apr. 8, 2016

(86) PCT No.: PCT/JP2016/061625
§ 371 (c)(1),
(2) Date: Oct. 6, 2017

(87) PCT Pub. No.: WO2016/163552
PCT Pub. Date: Oct. 13, 2016

(65) Prior Publication Data
US 2018/0099922 A1 Apr. 12, 2018

(30) Foreign Application Priority Data

Apr. 9, 2015 (JP) .................. 2015-080380

(51) Int. Cl.
C07C 47/02 (2006.01)
C07C 67/62 (2006.01)
C07C 69/653 (2006.01)

(52) U.S. Cl.
CPC ............ C07C 69/653 (2013.01); C07C 67/62 (2013.01); C07C 47/02 (2013.01)

(58) Field of Classification Search
CPC ................ C07C 69/653; C07C 67/62
USPC ....................................................... 560/223
See application file for complete search history.

(56) References Cited

U.S. PATENT DOCUMENTS

| 6,179,966 B1 | 1/2001 | Shimizu et al. |
| 6,458,989 B1 | 10/2002 | Aichinger et al. |

| 2007/0129564 A1 | 6/2007 | Schwalm |
| 2012/0059187 A1 | 3/2012 | Ishii et al. |
| 2012/0283468 A1 | 11/2012 | Kreis et al. |

FOREIGN PATENT DOCUMENTS

| EP | 1 041 062 | 10/2000 |
| EP | 2 135 656 | 12/2009 |
| EP | 2 415 751 | 2/2012 |
| EP | 2 540 700 | 1/2013 |
| GB | 1017346 | 1/1966 |
| GB | 1 489 536 | 10/1977 |
| GB | 2 285 983 | 8/1995 |
| JP | 48-103512 | 12/1973 |
| JP | 48103512 A * | 12/1973 |
| JP | 60-158136 | 8/1985 |
| JP | 60158136 A * | 8/1985 |
| JP | 07252477 A * | 1/1995 |
| JP | 7-252477 | 10/1995 |
| JP | 2002-509904 | 4/2002 |
| JP | 2002509904 A * | 4/2002 |
| JP | 2011-1340 | 1/2011 |
| JP | 2012-530756 | 12/2012 |
| WO | 00/55279 | 9/2000 |

OTHER PUBLICATIONS

International Search Report dated Jul. 12, 2016 in International (PCT) Application No. PCT/JP2016/061625.
Extended European Search Report dated Oct. 29, 2018 in corresponding European patent application No. 16776718.5.

* cited by examiner

*Primary Examiner* — Deborah D Carr
(74) *Attorney, Agent, or Firm* — Wenderoth, Lind & Ponack, L.L.P.

(57) ABSTRACT

An object of the present invention is to provide a method for stabilizing an acrylic acid derivative, and a composition containing an acrylic acid derivative in which the acrylic acid derivative is stabilized. The present invention provides a composition comprising: (A) an acrylic acid derivative represented by Formula (I):

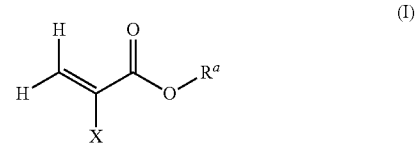

(I)

(wherein $R^a$ represents alkyl, fluoroalkyl, aryl that may have one or more substituents, or hydrogen; and X represents fluorine, alkyl, perfluoroalkyl, or hydrogen); and (B) aldehyde, wherein the content of acrylic acid derivative (A) is 30% (w/w) or more.

6 Claims, No Drawings

COMPOSITION

TECHNICAL FIELD

The present invention relates to a composition (in particular, a composition containing an acrylic acid derivative), a method for stabilizing an acrylic acid derivative, and the like.

BACKGROUND ART

Acrylic acid derivatives are widely used for (1) materials of water absorbing polymers, (2) materials of acrylic resins as a substitute for inorganic glass for use in window materials for buildings and vehicles, coverings for lighting equipment, lantern signs, road signs, daily necessities, office supplies, crafts, windscreens of watches, and the like, and (3) acrylic resin coating materials. Among acrylic acid derivatives, fluorine-containing acrylic acid derivatives are useful as synthetic intermediates of pharmaceuticals (e.g., antibiotics), synthetic intermediates for sheath materials of optical fibers, synthetic intermediates of coating materials, synthetic intermediates of semiconductor resist materials, and monomers of functional polymers.

Examples of known methods for producing an acrylic acid derivative include a method of producing an acrylic acid derivative by oxidizing isobutylene or propylene, and a method of producing an acrylic acid derivative using ethylene, propyne, or the like as a starting material using a transition metal catalyst.

Further, as examples of methods for producing a fluorine-containing acrylic acid derivative, for example, Patent Document 1 discloses a method of reacting a 2-fluoropropionic ester with a nitrogen-bromine-bond-containing brominating agent in the presence of a radical initiator, and Patent Document 2 discloses a process for converting a 3-halo-2-fluoropropionic acid derivative to a substituted 2-fluoroacrylic acid derivative in the presence of at least one kind of base and at least one kind of polymerization inhibitor.

CITATION LIST

Patent Documents

Patent Document 1: JP2011-001340A
Patent Document 2: JP2012-530756A

SUMMARY OF INVENTION

Technical Problem

Since an acrylic acid derivative contains active unsaturated bond due to its structure, it is unstable against external stimuli such as heat, light, and oxygen, and may easily change into an oligomer or a polymer by a polymerization reaction or the like.

Therefore, a method for stabilizing an acrylic acid derivative, and a composition containing an acrylic acid derivative in which the acrylic acid derivative is stabilized, have been in demand.

An object of the present invention is to provide a method for stabilizing an acrylic acid derivative, and a composition containing an acrylic acid derivative in which the acrylic acid derivative is stabilized.

Solution to Problem

The inventors of the present invention conducted extensive research to solve the above problem and found that it can be solved by a composition comprising:

(A) an acrylic acid derivative represented by Formula (I):

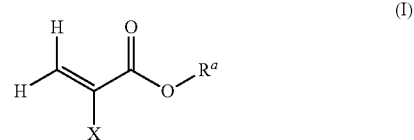

(wherein $R^a$ represents alkyl, fluoroalkyl, aryl that may have one or more substituents, or hydrogen; and X represents fluorine, alkyl, perfluoroalkyl, or hydrogen); and (B) aldehyde, wherein the content of acrylic acid derivative (A) is 30% (w/w) or more.

With this finding, the inventors completed the present invention.

The present invention includes the following aspects.

Item 1.

A composition comprising:

(A) an acrylic acid derivative represented by Formula (I):

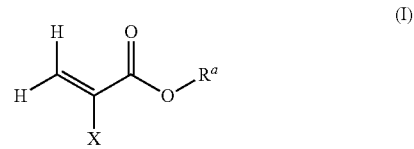

(wherein $R^a$ represents alkyl, fluoroalkyl, aryl that may have one or more substituents, or hydrogen; and X represents fluorine, alkyl, perfluoroalkyl, or hydrogen); and (B) aldehyde, wherein the content of acrylic acid derivative (A) is 30% (w/w) or more.

Item 2.

The composition according to Item 1, wherein the amount of aldehyde (B) is 0.1 mol or less, per mol of acrylic acid derivative (A).

Item 3.

The composition according to Item 1 or 2, wherein aldehyde (B) is $C_{1-20}$ linear saturated aldehyde.

Item 4.

The composition according to any one of Items 1 to 3, wherein $R^a$ is $C_{1-20}$ linear alkyl.

Item 5.

The composition according to any one of Items 1 to 4, wherein X is $C_{1-20}$ fluoroalkyl, fluorine, or chlorine.

Item 6.

The composition according to any one of Items 1 to 5, wherein X is fluorine.

Item 7.
A method for stabilizing
(A) an acrylic acid derivative represented by Formula (I):

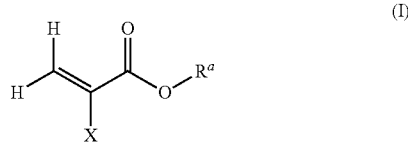

(wherein $R^a$ represents alkyl, fluoroalkyl, aryl that may have one or more substituents, or hydrogen; and X represents fluorine, alkyl, perfluoroalkyl, or hydrogen,
the method comprising making the acrylic acid derivative represented by Formula (I) coexist with aldehyde.
Item 8.
The method according to Item 7, wherein the amount of the aldehyde is 0.1 mol or less, per mol of the acrylic acid derivative represented by Formula (I).
Item 9.
The method according to Item 7 or 8, wherein the aldehyde is $C_{1-20}$ linear saturated aldehyde.
Item 10.
The method according to any one of Items 7 to 9, wherein $R^a$ is $C_{1-20}$ linear alkyl.
Item 11.
The method according to any one of Items 7 to 10, wherein X is $C_{1-20}$ fluoroalkyl, fluorine, or chlorine.
Item 12.
The method according to any one of Items 7 to 11, wherein X is fluorine.

Advantageous Effects of Invention

The composition of the present invention contains an acrylic acid derivative; in the composition, the acrylic acid derivative is stabilized.
The method of the present invention stabilizes an acrylic acid derivative.

DESCRIPTION OF EMBODIMENTS

Terms
The symbols and the abbreviations in this specification are to be interpreted as having the general meanings in the related technical field to which the present invention pertains, according to the context of this specification, unless otherwise specified.
In this specification, the term "comprise/contain" is intended to mean both "consist essentially of" and "consist of".
In this specification, "stabilization" of an acrylic acid derivative refers to preventing an acrylic acid derivative from changing into a different substance, such as a polymer.
In this specification, "alkyl" (the term "alkyl" encompasses the "alkyl" moiety in "fluoroalkyl" or the like) may be a cyclic, linear, or branched alkyl.
In this specification, "alkyl" may be, for example, a $C_{1-20}$, $C_{1-12}$, $C_{1-6}$, $C_{1-4}$, or $C_{1-3}$ alkyl.
In this specification, specific examples of "alkyl" include methyl, ethyl, propyl, isopropyl, butyl, isobutyl, sec-butyl, tert-butyl, pentyl, neopentyl, hexyl, and like linear or branched alkyls.

In this specification, specific examples of "alkyl" include cyclopropyl, cyclobutyl, cyclopentyl, cyclohexyl and like $C_{3-6}$ cyclic alkyls (cycloalkyls).
In this specification, "fluoroalkyl" refers to an alkyl in which at least one hydrogen is replaced by fluorine.
In this specification, the number of fluorines in the "fluoroalkyl" may be one or more (the maximum replaceable number from 1; e.g., 1 to 3, 1 to 6, or 1 to 12).
The "fluoroalkyl" encompasses perfluoroalkyl. The "perfluoroalkyl" refers to an alkyl in which all of the hydrogens are replaced by fluorines.
In this specification, examples of "fluoroalkyl" include $C_{1-20}$, $C_{1-12}$, $C_{1-6}$, $C_{1-4}$, and $C_{1-3}$ fluoroalkyls.
In this specification, the "fluoroalkyl" may be a linear or branched fluoroalkyl.
In this specification, specific examples of "fluoroalkyl" include fluoromethyl, difluoromethyl, trifluoromethyl, 2,2,2-trifluoroethyl, pentafluoroethyl, tetrafluoropropyl (e.g., $HCF_2CF_2CH_2$—), hexafluoropropyl (e.g., $(CF_3)_2CH$—), nonafluorobutyl, octafluoropentyl (e.g., $HCF_2CF_2CF_2CF_2CH_2$—), and tridecafluorohexyl.
In this specification, examples of "aryl" include phenyl and naphthyl.
In this specification, examples of "halogen" include fluorine, chlorine, bromine, and iodine.
In this specification, the "alkoxy" is an alkyl-O-group.
In this specification, examples of "acyl" include alkanoyl (i.e., alkyl-CO-group).
In this specification, examples of "ester" include alkyl-carbonyloxy (i.e., alkyl-CO—O-group), and alkoxycarbonyl (i.e., alkyl-O—CO-group).
Composition
The composition of the present invention comprises: (A) an acrylic acid derivative represented by Formula (I):

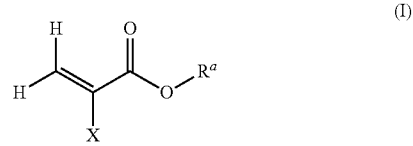

(wherein $R^a$ represents alkyl, fluoroalkyl, aryl that may have one or more substituents, or hydrogen; and X represents fluorine, alkyl, perfluoroalkyl, or hydrogen); and
(B) aldehyde,
wherein the content of acrylic acid derivative (A) is 30% (w/w) or more.
Acrylic Acid Derivative (A)
Each symbol in Formula (1) representing acrylic acid derivative (A) is explained below.
Preferable examples of the substituents of the "aryl that may have one or more substituents" represented by $R^a$ include fluorine, alkyl, alkoxy, acyl, ester, cyano, nitro, and fluoroalkyl. More preferable examples include fluorine.
The number of "the substituents" is preferably 0 (i.e., unsubstituted), 1, 2, or 3.
$R^a$ is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear alkyl.
X is $C_{1-20}$ (preferably $C_{1-12}$, more preferably $C_{1-6}$, further preferably $C_{1-4}$, further more preferably $C_{1-3}$, particularly preferably $C_1$ or $C_2$) fluoroalkyl, fluorine, or chlorine, and more preferably fluorine.

In Formula (I), preferably,
$R^a$ represents methyl or ethyl (more preferably methyl), and X is fluorine or chlorine (more preferably fluorine).

The composition of the present invention may comprise one or more kinds of acrylic acid derivative (A); however, the composition of the present invention preferably comprises only one kind of acrylic acid derivative (A).

Acrylic acid derivative (A) used in the present invention may be produced by a known method or a similar method thereof, or may be obtained from commercial suppliers.

Acrylic acid derivative (A) used in the present invention may be produced, for example, through the production methods disclosed in International Publication No. 2014/034906, JP2014-24755A, U.S. Pat. No. 3,262,968, and the like, or similar methods thereof.

The content of acrylic acid derivative (A) in the composition of the present invention is 30% (w/w) or more.

Generally, when the concentration of acrylic acid derivative (A) is high, unintended polymerization reaction or the like more easily occurs. However, in the composition of the present invention, even when the content of acrylic acid derivative (A) is high, acrylic acid derivative (A) is stable.

Further, the content of acrylic acid derivative (A) in the composition of the present invention is preferably 40% (w/w) or more, 50% (w/w) or more, 60% (w/w) or more, 70% (w/w) or more, 80% (w/w) or more, or 90% (w/w) or more.

The upper limit of the content of acrylic acid derivative (A) in the composition of the present invention is, for example, but not particularly limited to, 98% (w/w), 95% (w/w), or 90% (w/w). However, as it would be obvious to a person skilled in the art, the upper limit of the content of acrylic acid derivative (A) in the composition of the present invention may be limited depending on the amount of aldehyde (B) contained in the composition of the present invention.

Aldehyde (B)

Aldehyde (B) may be at least one member selected from the group consisting of aliphatic aldehydes, and aromatic aldehydes that may be substituted with at least one substituent.

The "aliphatic aldehyde" may be a linear or branched aliphatic aldehyde, and may be a saturated or unsaturated aliphatic aldehyde.

Aldehyde (B) is preferably $C_{1-20}$ (preferably $C_{1-12}$, more preferably $C_{1-6}$, further preferably $C_{1-4}$, further more preferably $C_{1-3}$, particularly preferably $C_1$ or $C_2$) linear saturated aldehyde.

In this specification, "aliphatic aldehyde" refers to, for example, a compound represented by formula: R—CHO (wherein R represents an aliphatic hydrocarbon group). The aliphatic hydrocarbon group represented by R is preferably an aliphatic hydrocarbon group.

In this specification, "aromatic aldehyde" refers to, for example, a compound represented by formula: R—CHO (wherein R represents aryl substituted with at least one substituent).

Specifically, aldehyde (B) is preferably one or more members (preferably one member) selected from the group consisting of formaldehyde, acetaldehyde, n-propylaldehyde, isopropylaldehyde, n-butylaldehyde, isobutylaldehyde, pivalaldehyde, n-pentylaldehyde, n-hexylaldehyde, n-heptylaldehyde, n-octylaldehyde, nonylaldehyde, decylaldehyde, undecylaldehyde, dodecylaldehyde, tridecylaldehyde, benzaldehyde, o-anisaldehyde, m-anisaldehyde, p-anisaldehyde, o-tolualdehyde, m-tolualdehyde, p-tolualdehyde and the like, and more preferably n-butylaldehyde.

Aldehyde (B) used in the present invention may be produced by a known method or a similar method, or may be obtained from commercial suppliers.

In the composition of the present invention, the content of aldehyde (B) is preferably 0.1 mol or less, more preferably 0.05 mol or less, and further preferably 0.02 mol or less, per mol of acrylic acid derivative (A).

In the composition of the present invention, even a very small amount of aldehyde (B) can stabilize acrylic acid derivative (A); however, in the composition of the present invention, the content of aldehyde (B) is, for example, 0.0005 mol or more, per mol of acrylic acid derivative (A).

In the composition of the present invention, the molar ratio of acrylic acid derivative (A) and aldehyde (B) is preferably 1:0.1 or less, more preferably in a range of 1:0.0005 to 1:0.05, further preferably in a range of 1:0.0005 to 1:0.02.

Optional Components

The composition of the present invention may contain optional components in addition to acrylic acid derivative (A) and aldehyde (B). The optional components may be impurities that coexist with acrylic acid derivative (A) or aldehyde (B) prepared for the production of the composition of the present invention.

Examples of the optional components include water and organic solvents.

In the composition of the present invention, since acrylic acid derivative (A) is stabilized by aldehyde (B), the significance of using a polymerization inhibitor for the purpose of stabilizing acrylic acid derivative (A) is small; however, the composition of the present invention may contain a polymerization inhibitor as an optional component.

As a method for preventing unintended polymerization reaction or the like, a method of using a polymerization inhibitor, such as the polymerization inhibitor disclosed in Patent Document 2, has been known. However, acrylic acid derivative (A) may be exposed to various conditions, for example, upon storage or at the time of use. Since the boiling points of versatile polymerization inhibitors greatly differ from that of an acrylic acid derivative, it is often difficult to make them coexist with an acrylic acid derivative. In this case, the polymerization inhibitors cannot fully exhibit the function.

When the composition of the present invention is exposed to a gas phase, the gas phase may be, but not limited to, for example, an inert gas such as nitrogen.

Stability of the Composition of the Present Invention

In the composition of the present invention, acrylic acid derivative (A) is stabilized. More specifically, acrylic acid derivative (A) contained in the composition of the present invention has high stability.

Specifically, for example, acrylic acid derivative (A) in the composition of the present invention is prevented from changing into a polymer or the like, compared with a case in which acrylic acid derivative (A) does not coexist with aldehyde (B).

In the present invention, the change of acrylic acid derivative (A) into a different substance may be analyzed, for example, using NMR analysis or the like. Further, for example, the change of acrylic acid derivative into a polymer may be easily detected by observation of a change of a colorless transparent solution of acrylic acid derivative into a solid, or the like.

When the composition of the present invention is allowed to stand at 40° C. for 90 minutes, the percentage of decrease in the content of acrylic acid derivative (A) defined by the formula below is preferably less than 90%, more preferably less than 70%, further preferably less than 50%, furthermore preferably less than 40%.

$$\text{The percentage of decrease in content of acrylic acid derivative } (A)\ (\%) = (W_0 - W_1)/W_0 \quad \text{Formula: 5}$$

In the formula, $W_0$ represents the content of acrylic acid derivative (A) (wt %) before acrylic acid derivative (A) is allowed to stand at 40° C. for 90 minutes, and $W_1$ represents the content (wt %) of acrylic acid derivative (A) after acrylic acid derivative (A) is allowed to stand at 40° C. for 90 minutes.

In the composition of the present invention, acrylic acid derivative (A) is stabilized by the coexistence with aldehyde (B).

A method for making an acrylic acid derivative coexist with a polymerization inhibitor has been known as a means for stabilizing an acrylic acid derivative.

However, since acrylic acid derivative (A) may be exposed to various conditions, for example, upon storage or at the time of use, the coexistence of a polymerization inhibitor with an acrylic acid derivative may be difficult in some cases.

In this case, the polymerization inhibitor cannot fully exhibit the function.

In contrast, since aldehyde (B) may have a boiling point similar to that of acrylic acid derivative (A), it is easy to make aldehyde (B) coexist with acrylic acid derivative (A). Therefore, acrylic acid derivative (A) in the composition of the present invention is stable under various conditions.

Production Method

The composition of the present invention may be produced by mixing acrylic acid derivative (A), aldehyde (B), and optional components using, for example, a usual method such as stirring.

Some or all of aldehyde (B) may be contained as an impurity or an additive in acrylic acid derivative (A) prepared for the production of the composition of the present invention.

Method for Stabilizing Acrylic Acid Derivative (A)

The method for stabilizing the acrylic acid derivative (acrylic acid derivative (A)) represented by Formula (I) of the present invention comprises making acrylic acid derivative (A) coexist with aldehyde (aldehyde (B)).

The method for making acrylic acid derivative (A) coexist with aldehyde (B) is not particularly limited. Examples of the method include:
[1] a method of mixing acrylic acid derivative (A) and aldehyde (B);
[2] a method of producing aldehyde (B) in a system containing acrylic acid derivative (A);
[3] a method of producing acrylic acid derivative (A) in a system containing aldehyde (B); and
[4] a method of individually producing acrylic acid derivative (A) and aldehyde (B) in a single system.

The same explanation of acrylic acid derivative (A) as that regarding the composition of the present invention can be applied to acrylic acid derivative (A) used in the method for stabilizing acrylic acid derivative (A) of the present invention.

The same explanation of amide (B) as that regarding the composition of the present invention can be applied to aldehyde (B) used in the method for stabilizing acrylic acid derivative (A) of the present invention.

In the method for stabilizing acrylic acid derivative (A) of the present invention, preferably, aldehyde (B) is used at a predetermined molar ratio relative to acrylic acid derivative (A). The molar ratio is as described above regarding the composition of the present invention.

The details of the method for stabilizing acrylic acid derivative (A) including the above matters can be understood from the above explanation regarding the composition of the present invention.

EXAMPLES

The present invention is described below in more detail with reference to Examples. However, the present invention is not limited to these Examples.

The Examples below confirmed that 2-fluoroacrylic acid methyl ester purified by distillation did not contain n-butylaldehyde (more specifically, the content of n-butylaldehyde was 0.0 mol % relative to the 2-fluoroacrylic acid methyl ester).

Example 1

As an acrylic acid derivative, 1.1 g of 2-fluoroacrylic acid methyl ester purified by distillation was placed in an airtight-closable test tube having an inner volume of 10 mL. Subsequently, 0.76 mg of n-butylaldehyde was added thereto so that its amount was 0.1 mol % based on the 2-fluoroacrylic acid methyl ester, thereby preparing a sample of Example 1. Regarding the appearance and the characteristics of the composition sample, the composition sample was a colorless and transparent liquid.

The stability of the sample was evaluated using the method below.

Method for Evaluating Stability of Composition

The test tube containing the sample was allowed to stand at a temperature of 40° C. for 90 minutes, and the amount (%) of the remaining 2-fluoroacrylic acid methyl ester was analyzed by $^{19}$F-NMR. Further, the characteristics of the sample after the sample was allowed to stand at 40° C. for 90 minutes were observed. Table 1 shows the results.

Example 2

The sample of Example 2 was prepared using the same method as that of Example 1, except that the amount of n-butylaldehyde was changed to 1 mol % based on the 2-fluoroacrylic acid methyl ester. Regarding the appearance and the characteristics of the composition sample, the composition sample was a colorless and transparent liquid.

The stability of the 2-fluoroacrylic acid methyl ester in this sample was evaluated using the same method as in Example 1. Table 1 shows the results.

Comparative Example 1

The sample of Comparative Example 1 was prepared using the same method as that of Example 1, except that n-butylaldehyde was not added (more specifically, the amount of n-butylaldehyde was 0.0 mol % relative to the 2-fluoroacrylic acid methyl ester). The stability of the 2-fluoroacrylic acid methyl ester in this sample was evaluated using the same method as in Example 1. Table 1 shows the results. Generation of a solid was observed; thus, it was confirmed that a polymer was produced from the 2-fluoroacrylic acid methyl ester. Under the conditions in this Example (n-butylaldehyde was not added), the 2-fluoroacrylic acid methyl ester was very easily polymerized. Therefore, the amount of the remaining 2-fluoroacrylic acid methyl ester was 0%.

TABLE 1

|  |  | 2-fluoroacrylic acid methyl ester: n-butylaldehyde (mol:mol) | Amount of remaining 2-fluoroacrylic acid methyl ester [%] ($^{19}$FNMR) | Percentage of decrease of 2-fluoroacrylic acid methyl ester [%] | Characteristics of sample (after the sample was allowed to stand at 40° C. for 90 minutes) |
|---|---|---|---|---|---|
| Example | 1 | 1:0.001 | 64.2 | 35.8 | Colorless transparent liquid |
|  | 2 | 1:0.01 | 25.1 | 74.9 | Colorless transparent liquid |
| Comparative Example | 1 | 1:0 | 0 | 100 | Solid |

The invention claimed is:

1. A composition comprising:
   (A) an acrylic acid derivative represented by Formula (I):

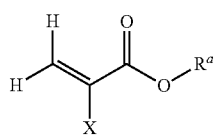

wherein $R^a$ represents alkyl, fluoroalkyl, aryl that may have one or more substituents, or hydrogen; and X represents fluorine; and
   (B) aldehyde,
   wherein the content of acrylic acid derivative (A) is 30% (w/w) or more.

2. The composition according to claim 1, wherein the amount of aldehyde (B) is 0.1 mol or less, per mol of acrylic acid derivative (A).

3. The composition according to claim 1, wherein aldehyde (B) is $C_{1-20}$ linear saturated aldehyde.

4. The composition according to claim 1, wherein $R^a$ is $C_{1-20}$ linear alkyl.

5. A method for stabilizing an acrylic acid derivative represented by Formula (I):

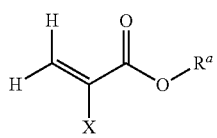

wherein $R^a$ represents alkyl, fluoroalkyl, aryl that may have one or more substituents, or hydrogen; and X represents fluorine,
   the method comprising making the acrylic acid derivative represented by Formula (I) coexist with aldehyde.

6. The method according to claim 5, wherein the amount of the aldehyde is 0.1 mol or less, per mol of the acrylic acid derivative represented by Formula (I).

* * * * *